United States Patent [19]

Warncke

[11] Patent Number: 4,583,964
[45] Date of Patent: Apr. 22, 1986

[54] METHOD AND APPARATUS FOR PRODUCING A CYLINDRICAL PACKING TUBE WHICH IS OPEN AT ONE END AND CLOSED AT THE OTHER

[75] Inventor: Niels Warncke, Mettmann-Metzkausen, Fed. Rep. of Germany

[73] Assignee: J&J G.m.b.H., Dusseldorf, Fed. Rep. of Germany

[21] Appl. No.: 571,875
[22] PCT Filed: May 4, 1983
[86] PCT No.: PCT/DE83/00080
§ 371 Date: Jan. 5, 1984
§ 102(e) Date: Jan. 5, 1984
[87] PCT Pub. No.: WO83/03964
PCT Pub. Date: Nov. 24, 1983

[30] Foreign Application Priority Data

May 14, 1982 [DE] Fed. Rep. of Germany ....... 3218331

[51] Int. Cl.[4] .............................................. B21D 5/08
[52] U.S. Cl. .................................... 493/308; 493/303; 493/108; 493/960; 493/930; 493/212; 229/87 R; 604/904
[58] Field of Search ............... 493/308, 108, 274, 304, 493/305, 960, 303, 930, 237, 212, 377, 462; 604/904; 206/438; 229/87 R

[56] References Cited

U.S. PATENT DOCUMENTS

| | | | |
|---|---|---|---|
| 905,844 | 12/1908 | Chesney | 493/308 |
| 931,269 | 8/1909 | Chesney | 493/303 |
| 2,370,079 | 2/1945 | Schmidt | 493/212 |
| 2,431,537 | 11/1947 | Bogoslowsky | 493/308 |
| 2,440,391 | 4/1948 | Bogoslowsky | 493/308 |
| 2,691,856 | 10/1954 | Jensen et al. | 493/377 |
| 2,780,379 | 2/1957 | Ferguson | 493/377 |
| 3,856,143 | 12/1974 | Simon et al. | 206/438 |
| 3,883,388 | 5/1975 | Amberg et al. | 493/108 |

FOREIGN PATENT DOCUMENTS 499611  1/1939  United Kingdom ............... 493/308

Primary Examiner—Francis S. Husar
Assistant Examiner—David B. Jones
Attorney, Agent, or Firm—Jason Lipow

[57] ABSTRACT

A method and an apparatus are indicated for the production of a cylindrical packing tube which is open at one end and closed at the other, is made from deformable tear-resistant packing material and is intended, in particular, for tampons used in female hygiene, wherein a portion of the packing material is drawn by suction onto a winding spindle provided with suction apertures and through the rotation of the winding spindle is wrapped around the latter, while the overlapping ends of the portion are joined together to form the packing tube, whose end projecting beyond the winding spindle is closed, whereupon the packing tube is removed from the winding spindle. The method is characterized in that that end of the cylindrical packing tube which projects beyond the winding spindle is held fast and during the rotation of the winding spindle is closed so as to form a twist. The method permits the production of a uniform closure pattern of the packing tube irrespective of the shape of the tampon insertion end.

7 Claims, 10 Drawing Figures

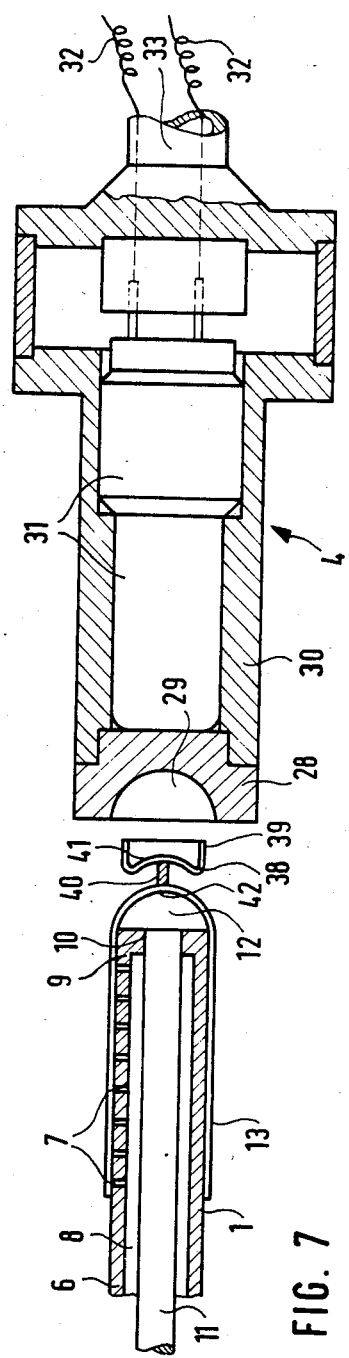
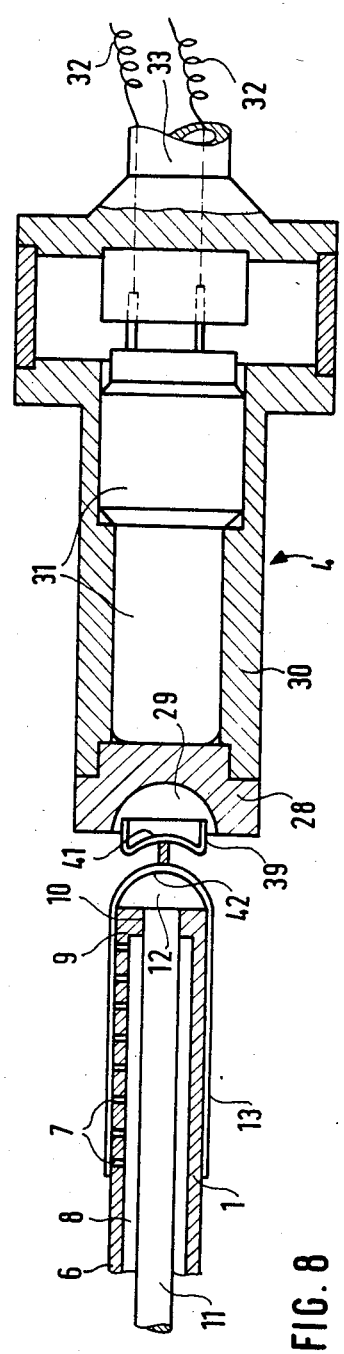

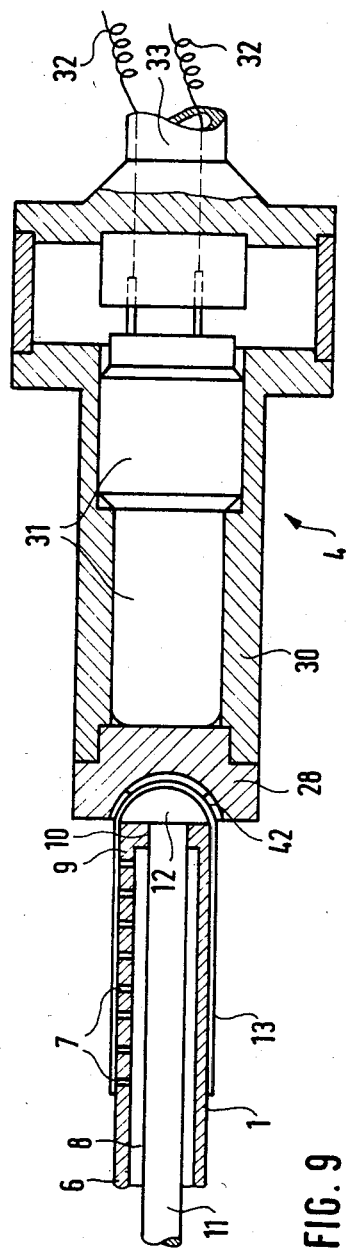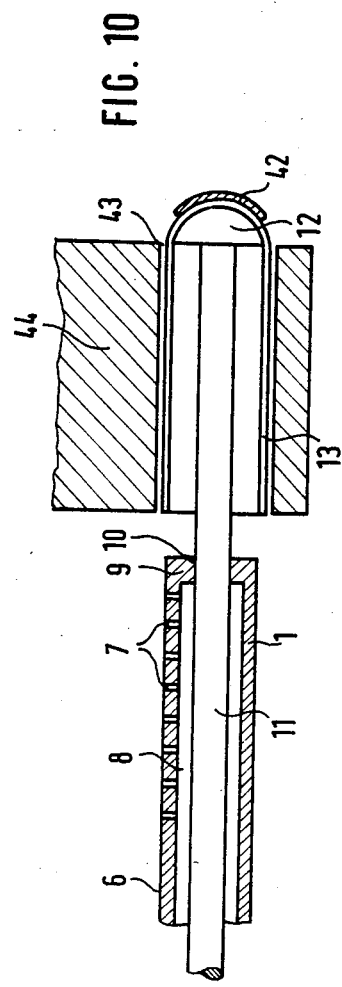

METHOD AND APPARATUS FOR PRODUCING A CYLINDRICAL PACKING TUBE WHICH IS OPEN AT ONE END AND CLOSED AT THE OTHER

The invention relates to a method for producing a cylindrical packing tube which is open at one end and closed at the other and is made from deformable tear-resistant packing material, and to an apparatus for carrying out this method.

There are numerous mass-produced articles which have to be packed until used for the purpose for which they are intended, in order to protect them against soiling and other harmful influences. These include, for example, tampons for feminine hygiene, which are packed individually in cylindrical packing tubes. In this connection it must be borne in mind that such tampons are frequently produced by compressing on all sides a moisture-absorbing material, so that before they are used they tend to expand again in all directions. It is therefore expedient for each tampon to be surrounded positively by a tear-resistant packing material.

From German Patent Specification No. 1,955,600 a method and an apparatus are known for closing, in a shape-retaining manner, at least one end of a packing tube, particularly for tampons for female hygiene. One still open end of a cylindrical packing tube containing a tampon, the rounded insertion end of which faces the open end of the packing tube, is in this case closed by means of a twisting device. This operation consists in that the twisting device grips the packing material at the open end of the packing tube and turns it while the packing tube remains stationary. A twist is thus formed at this end of the packing tube, and the rosette of this tube, which at first projects, is pressed against the packing tube and then flattened. The end of the packing tube closed in this manner then corresponds in shape to the rounded insertion end of the packed tampon.

With this procedure, the use of a heat-sealable film coated on both sides, for example of cellulose hydrate or regenerated cellulose (obtainable under the trade mark "CELLOPHAN"), may have the consequence that this film is by mistake sealed to the insertion end of the tampon and is then difficult to remove when the tampon is to be used.

In addition, with this type of tube closure, different closure patterns are obtained, depending on the shape of the rounded end of the tampon. Nevertheless, a uniform closure pattern is desirable, which is not dependent on the shape of the end of the tampon.

The problem underlying the invention is that of providing a method and an apparatus which permit the production of a cylindrical packing tube which is open at one end and closed at the other, is made from deformable tear-resistant packing material and is intended, in particular, for tampons used in female hygiene, wherein a high speed of production is achieved, and a reliable aesthetically perfect closure of the respective end of the packing tube is obtained. In addition, it should be possible to use a heat-sealable film coated on both sides as packing material, and it should be ensured that the objects which are to be packed, e.g. tampons, can be packed positively in the packing tube without undesirable sticking to the packing material.

In order to solve this problem, the starting point of the invention is a method in which a portion of the packing material is drawn by suction onto a winding spindle provided with suction apertures and through the rotation of the winding spindle is wrapped around the latter, while the overlapping ends of the portion are joined together to form the packing tube, whose end projecting beyond the winding spindle is closed, whereupon the packing tube is removed from the winding spindle; the method according to the invention is characterised in that that end of the cylindrical packing tube which projects beyond the winding spindle is held fast and is closed during the rotation of the winding spindle so as to form a twist.

According to a further development of the method, the overlapping ends of the portion of packing material are joined by heat sealing. In this way, a packing tube durably closed on its periphery is obtained by a short process step.

In a preferred embodiment of the method, the axial distance between the winding spindle and a twisting head during the formation of the twist is shortened in accordance with the decrease in length of that end of the packing tube which projects beyond the winding spindle, by a coaxial movement of the winding spindle and/or of the twisting head. On the one hand this brings about a more extensive twisting of the open end of the packing tube and accordingly a firmer closure at that end, while on the other hand the tearing of the packing material through excessive tensile stressing during the twisting operation is avoided.

It is advantageous for the twist rosette formed by the twisting of one end of the packing sleeve to be pressed onto the packing sleeve in the direction of the end face of the winding spindle and thereupon to be flattened positively against the said tube. This not only counteracts the tendency of various packing materials to untwist slowly a twist formed on them, but also forms an aesthetically attractive packing tube which is to a large extent adapted to the shape of the object packed and has no projecting packing parts.

In certain cases it is advantageous for the closed end of the packing tube to be made in the form of a round dome. This procedure is for example suitable for packing tubes for tampons having a rounded insertion end.

For the purpose of carrying out the method according to the invention and thus of solving the problem indicated above, use is made of an apparatus having a winding spindle which is provided with suction apertures distributed over part of its periphery and over its axial length and which is mounted on the end of a hollow shaft sealed at its end face and adapted to be connected to a suction air source, while a closing device for the cylindrical end of the packing tube, which end projects beyond this end of the winding spindle, is associated with the free end of the winding spindle.

The apparatus is characterised according to the invention by the combination of the features that at the free end of the winding spindle a push-off head for the packing tube is disposed for axial movement relative to the winding spindle, that the closing device for one end of the packing tube is a twisting device which is coaxially movable relative to the push-off head of the winding spindle and whose dolly spindle has a smaller diameter than that of the winding spindle, while a plurality of clamp jaws are disposed around the periphery of the dolly spindle in such a manner as to be pivotable in planes which are radial in relation to the axis of rotation of the dolly spindle.

The apparatus is preferably so constructed that the push-off head is disposed at the free end of a push-off rod which extends coaxially through a suction chamber in the winding spindle. The push-off head is in this way movable axially relative to the winding spindle for the purpose of removing the packing tube from the winding spindle in a simple manner.

It has been found advantageous for the push-off head to have at most the same diameter as the winding spindle. It is thus ensured that, after the packing tube has been pushed off the winding spindle, the push-off head can easily be extracted from the packing tube.

In some cases it is advantageous for the push-off head to have the shape of a spherical calotte. This enables a round dome to be formed at one end of the packing tube, which is for example desirable in the case of the packing of tampons having a rounded insertion end.

According to an expedient embodiment of the apparatus, the push-off head has axially associated with it a reciprocatable pressing head, whose pressing surface matches the surface of the push-off head. As a result, on the one hand the twist rosette is joined to the packing tube in such a manner that the twist can no longer open spontaneously, while on the other hand a substantially smooth-surfaced and optically attractive external contour of the packing tube is obtained in this manner.

The pressing surface of the pressing head is preferably disposed on a shaped member which is adapted to be heated by an electric resistance heating element in the pressing head. The pressing surface of the pressing head can thus be brought rapidly to the temperature desired for the pressing operation. By varying the electric heating current, moreover, the temperature of the pressing head can be adapted in a simple manner to the sealing properties of the packing material.

In another embodiment of the apparatus a radially feedable heat-sealing jaw is associated with the winding spindle. This makes it possible to obtain within a short time a durable connection of the ends of the packing material which overlap in the peripheral direction of the packing tube. Since, for this purpose, a relatively slight overlapping of these ends is achieved, this embodiment helps to save packing material.

The invention is explained more fully below with the aid of an example of embodiment of an apparatus for carrying out the method, which apparatus is diagrammatically illustrated in the drawing, in which:

FIG. 7 shows the winding mandrel which is shown in FIG. 6 and which carries the packing tube with a twist rosette at one end, and also a longitudinal section through a pressing head axially associated with the winding spindle;

FIG. 8 shows the arrangement shown in FIG. 7, but with a shorter axial distance between the winding spindle and the pressing head;

FIG. 9 shows the arrangement shown in FIG. 8, but with the pressing head resting against the end face of the winding spindle, and FIG. 10 shows the winding mandrel shown in FIG. 9 after the packing tube has been pushed off it by the push-off head and transferred to a conveyor means, partly in section.

Figure 1:
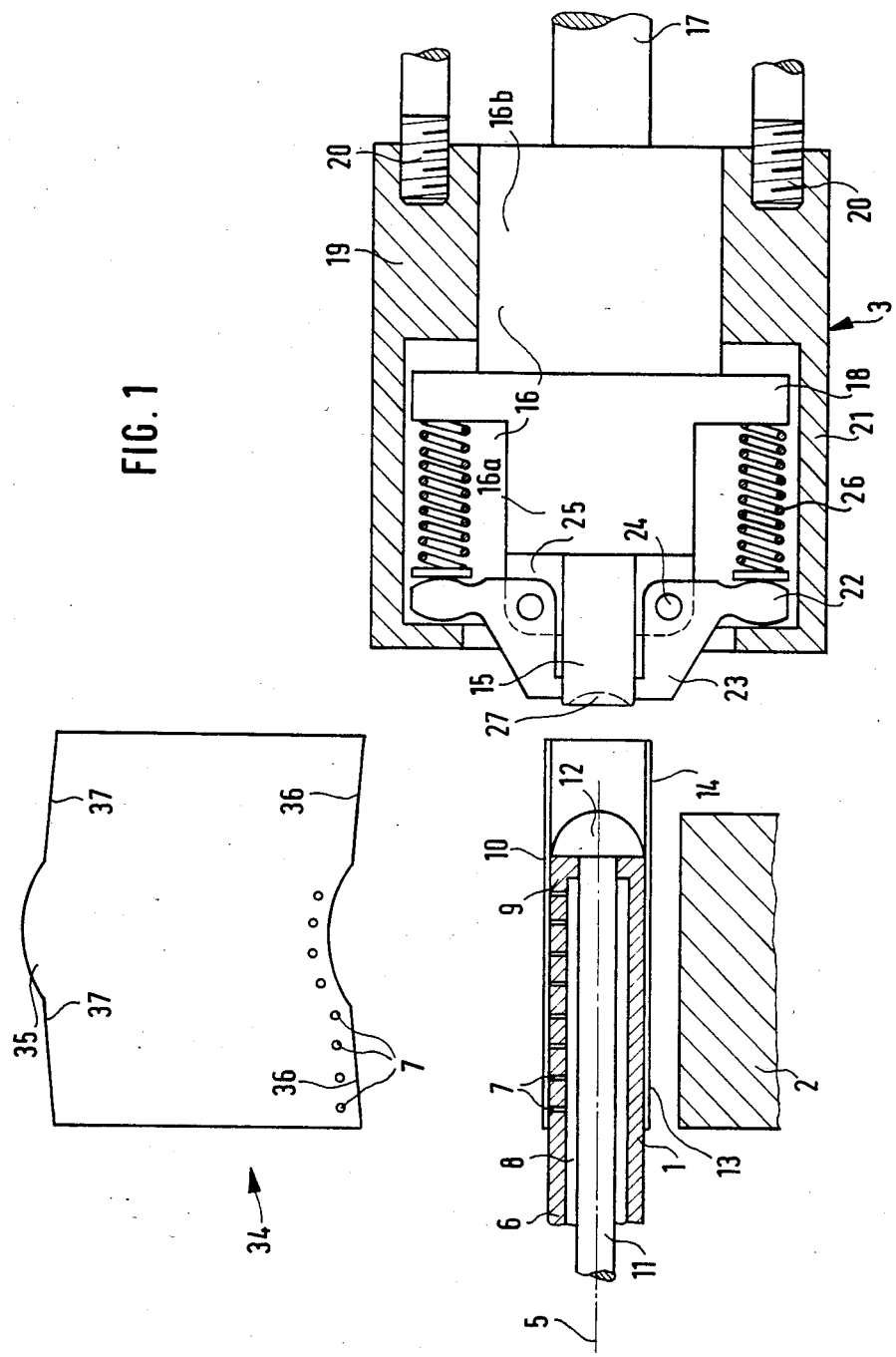
FIG. 1 shows, in respective longitudinal axial sections, the apparatus with a winding spindle on which a packing tube is mounted and with a heat-sealing jaw, and also a twisting head coaxial to the winding spindle, as well as, in elevation, a portion of packing material.

According to FIGS. 1 to 6, the apparatus comprises mainly a cylindrical winding spindle 1, a heat sealing jaw 2 adapted to be radially fed towards the spindle 1, and a twisting head 3 adapted to move coaxially relative to the winding spindle 1, and, according to FIGS. 7 to 9, it also comprises a pressing head 4 adapted to move coaxially relative to the winding spindle 1.

The winding spindle 1 mounted rotatably about its longitudinal axis 5 is seated on one end of a hollow shaft 6 and on its periphery, along a generatrix, is provided with suction apertures 7. These suction apertures are connected by way of a coaxially shaped suction chamber 8 in the interior of the winding spindle 1 to a suction air source (not shown).

According to FIG. 1, the suction apertures 7 are disposed in a radial plane of the winding spindle 1. In such a case a portion 34 of a deformable tear-resistant packing material, which is to be wound, is normally substantially rectangular.

The portion 34 may, however, also have a different contour, as shown for example in FIG. 1. With this contour the edges of the ends 36, 37 of the portion 34, although parallel to one another, do not however form straight lines. In addition, at the end 37 a gripping tab 35 is provided, which subsequently will facilitate the tearing-open of the finished packing tube. The end 36 of the portion 34 has a cutout corresponding to the gripping tab 35, since the portion 34 has been cut off from a longer strip of packing material by means of a rotary cutter.

In the case of the contour of the portion 34, shown in FIG. 1, the suction apertures 7 expediently have an arrangement corresponding to this contour, as indicated at the end 36 of the portion 34 with the aid of small circles 7. In the case of other contours, the suction apertures are correspondingly arranged differently.

At its free end 9, which at the same time is the free end 9 of the winding spindle, the hollow shaft 6 is sealed. This sealing is effected with the aid of a push-off rod 11 which is coaxially movable and positively guided by a coaxial opening 10 at the end 9 of the winding spindle 1, and/or by a push-off head 12 mounted on the end of the push-off rod 11.

According to FIGS. 1 to 10, the push-off head 12 has the shape of a spherical calotte, and its diameter is slightly smaller than the diameter of the winding spindle 1. However, other spherical calottes or different shapes are possible for the design of the push-off head 12. Its diameter may also be smaller than shown.

During use, the winding spindle 1 intermittently carries a packing tube 13, the open end 14 of which projects beyond the winding spindle 1 and the push-off head 12 in the direction of the longitudinal axis 5 of the winding spindle 1 and at the same time faces an axially disposed dolly spindle 15 of the twisting head 3.

The dolly spindle 15 is mounted at the end of a twisting shank 16 which is disposed coaxially relative to the longitudinal axis 5 of the winding spindle 1 and which is fixed to the end of a twisting shaft 17, which can be turned when required.

The twisting shank 16 has a thinner front portion 16a and a thicker rear portion 16b, between which portions an annular shoulder 18 projecting radially outward is disposed.

On the rear portion 16b of the twisting shank, remote from the winding spindle 1, a control ring 19 is mounted for displacement axially relative to the dolly spindle 15. A displacement of the control ring 19 is effected by corresponding operation of the guide rods 20 which are screwed into its rear side and are only partly shown in the drawing.

The control ring 19 surrounds at its front end facing the dolly spindle 15, with an annular shoulder 21 projecting radially inwards, lever arms 22 of clamp jaws 23 which are disposed around the periphery of the dolly spindle 15 in planes which are radial relative to the axis of rotation of the dolly spindle 15, these jaws being mounted on respective pivot pins 24 located on axial projections 25 on the front portion 16a of the twisting shank.

Spiral springs 26 are supported, in each case, between the lever arms 22 and the shank projection 18, the pressure of which springs, in a first position of the control ring 19, brings the clamp jaws 23 to bear against the dolly spindle 15 (FIGS. 1, 4 and 5), whereby the end 14 of the packing tube 13 is held fast. In a second position of the control ring 19, in which the spiral springs 26 are more heavily compressed, the said ring acts by means of the annular shoulder 21, on the lever arms 22 of the clamp jaws 23, which are thereby lifted off the dolly spindle 15 (FIGS. 2, 3 and 6) and free the end 14 of the packing tube 13.

The dolly spindle 15 has an end face 27 provided with a depression which has the shape of a spherical calotte and which matches the calotte shape of the push-off head 12.

According to FIG. 7, the pressing head 4 carries at its end facing the winding spindle 1 a shaped member 28 having a depression 29 matching the shape of the push-off head 12. The shaped member 28 is adapted to be heated by a resistance heating element 31 disposed in a shank 30 of the pressing head 4. Electric supply lines 32 for the resistance heating element 31 are taken inside a hollow pressing shaft 33 as far as the resistance heating element 31. The connection between the electric supply lines 32 and a current source (not shown) is made via slip rings (likewise not shown) and carbon brushes in contact with the latter.

The method according to the invention is carried out as follows:

According to FIG. 1, the portion 34 of the deformable, tear-resistant packing material is brought by one end tangentially up to the side of the winding spindle 1, where the suction apertures 7 are provided. The portion 34 is disposed on the winding spindle 1 in such a manner that the end 14 of the packing tube 13 which is to be formed projects beyond the free end 9 of the winding spindle 1.

By putting into action a suction air source (not shown) connected to the hollow shaft 6, a negative pressure is established in the interior of the winding spindle 1, in the suction chamber 8, and consequently in the region of the suction apertures 7. The portion 34 is thus drawn by suction, by one end, onto the winding spindle 1.

Through rotation of the winding spindle 1 and simultaneous pressing of the portion 34 onto the winding spindle 1 by means of a holding device (not shown), the portion 34 is wound around the winding spindle 1, so as to form a cylindrical packing tube 13.

The overlapping end 36, 37 of the portion 34, where they are supported by the winding spindle 1, are joined together by contact with the heat-sealing jaw 2.

Figure 2:
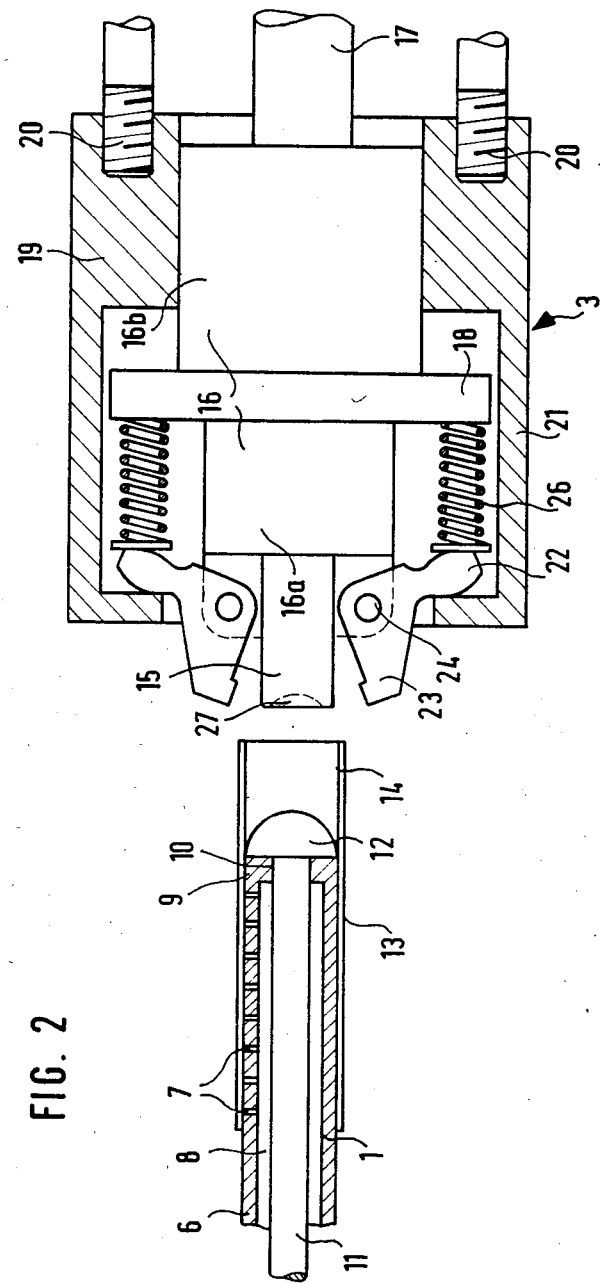
FIG. 2 shows the winding spindle and the twisting head shown in FIG. 1, but with the clamp jaws on the dolly spindle of the twisting head open.

According to FIG. 2, through the cooperation of the guide rods 20, the control ring 19 of the twisting head 3 is drawn back in the direction away from the winding spindle 1. The consequent pressure of the annular shoulder 21 on the lever arms 22 brings about the pivoting of the clamp jaws 23 away from the dolly spindle 15.

Figure 3:
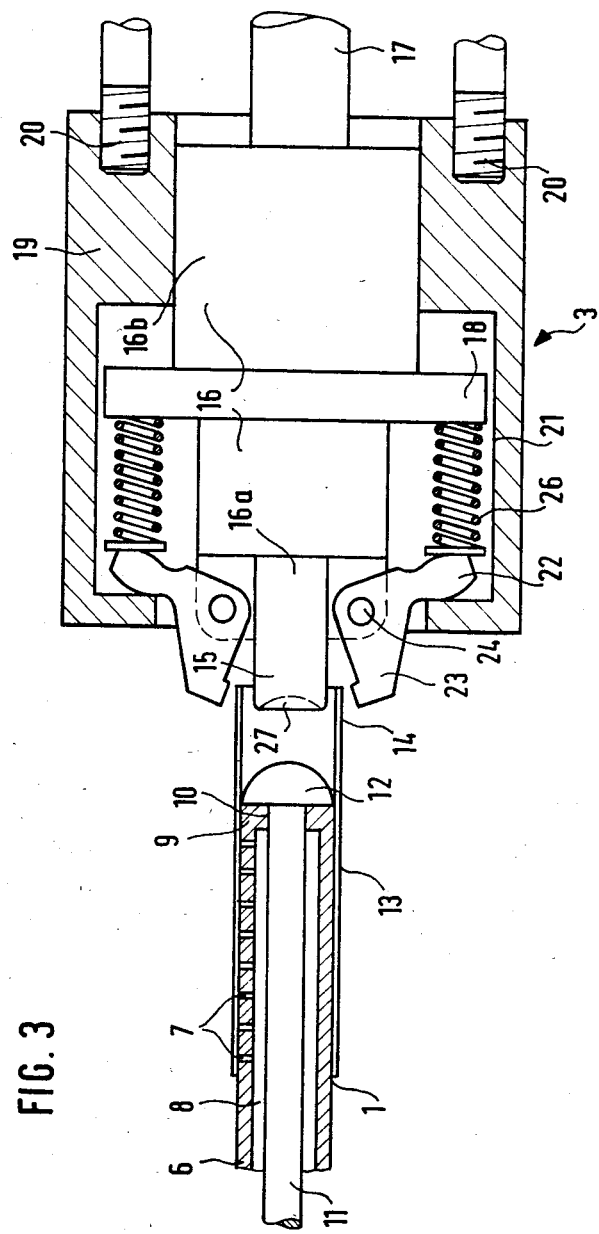
FIG. 3 shows the arrangement shown in FIG. 2, but with a shorter distance between the winding spindle and the dolly spindle of the twisting head.

In this position the winding spindle 1 and the twisting head 3 are brought close to one another, either through the movement of the winding spindle 1 and/or that of the twisting head 3, as shown in FIG. 3. At the same time the dolly spindle is inserted so far into the open end 14 of the packing tube 13 that this end 14 can be held fast by the clamp jaws 23 on the dolly spindle 15 when the said clamp jaws subsequently close.

Figure 4:
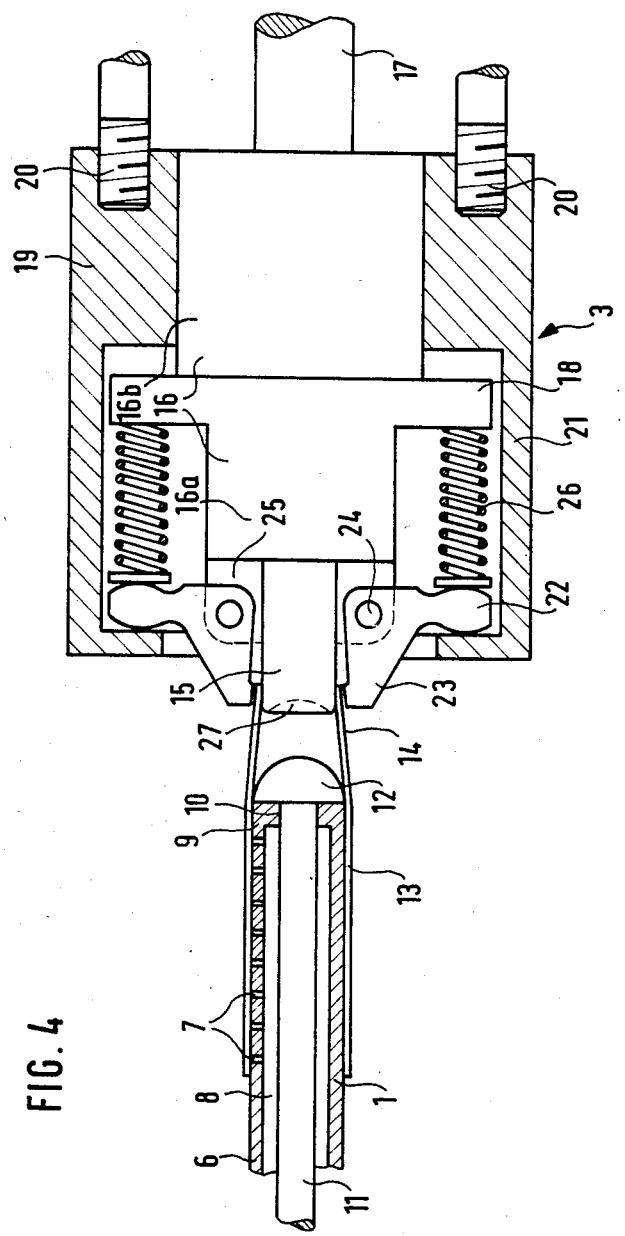
FIG. 4 shows the arrangement shown in FIG. 3, but with closed clamp jaws which, in conjunction with the dolly spindle of the twisting head, hold fast one end of the packing tube disposed on the winding spindle.

In order to close the clamp jaws, the control ring 19 is moved in the direction of the winding spindle. Through the action of the spiral springs 26, the clamp jaws 23 are thus brought into the closed position, as can be seen in FIG. 4.

Figure 5:
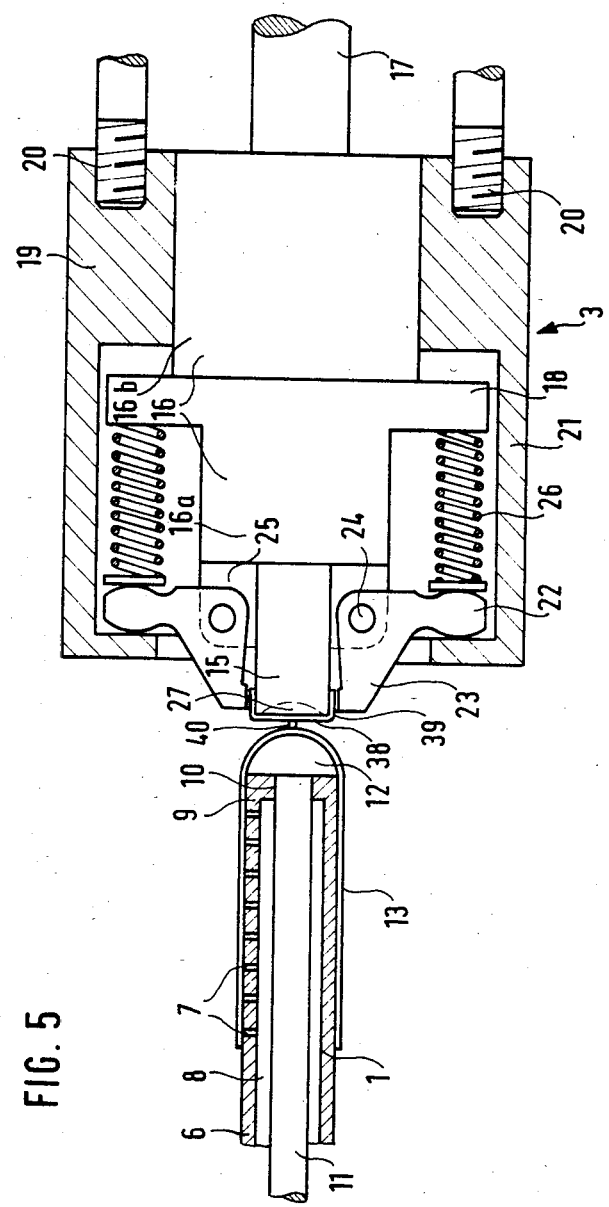
FIG. 5 shows the arrangement shown in FIG. 4, but after twisting of one end of the packing tube.

While the twisting head 3 is stationary, the winding spindle 1 together with the packing tube 13 is now turned, and the open end 14 of the packing tube 13 is closed by the formation of a twist 38 with a twist rosette 39 and a twist neck 40, as shown in FIG. 5. Alternatively, with the winding spindle 1 stationary, the twisting head 3 can be turned, or else both the winding spindle 1 and the twisting head 3 can be turned in opposite directions.

Figure 6:
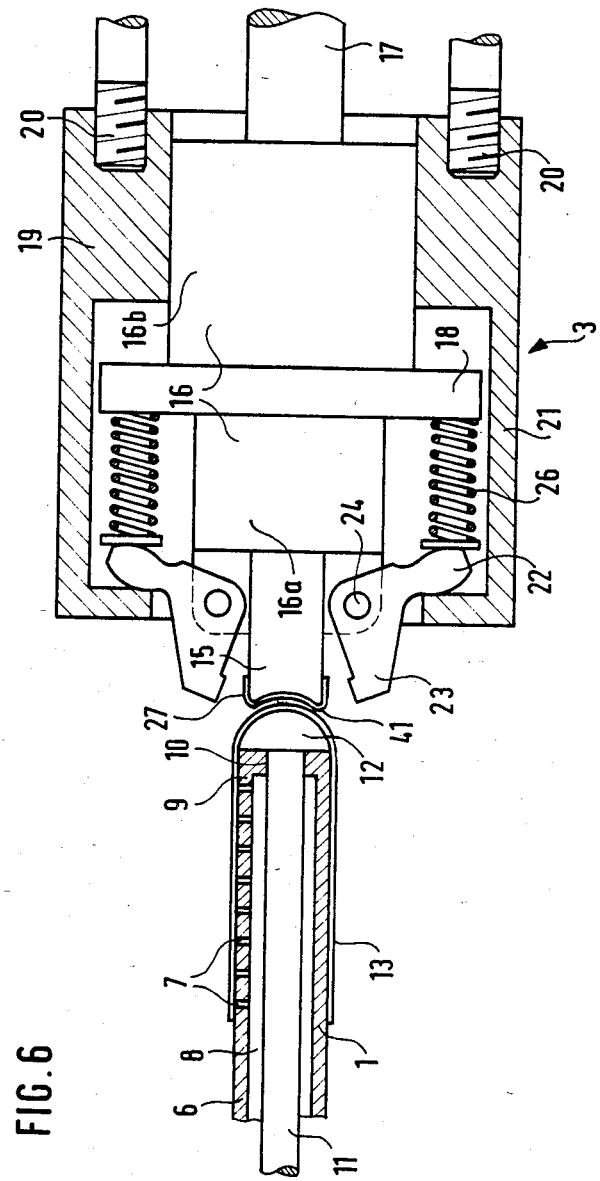
FIG. 6 shows the arrangement shown in FIG. 5, but with the clamp jaws open at the moment when the twist is pressed against the end face of the winding spindle.

According to FIG. 6, after the formation of the twist, renewed operation of the control ring 19 opens the clamp jaws 23 and at the same time the bottom 41 of the twist rosette 39 is pressed against the push-off head 12 by means of the dolly spindle 15. Since the end face 27 of the dolly spindle 15 corresponds to the shape of the push-off head 12, the bottom 41 of the twist rosette 39 is preshaped in accordance with the shape of the push-off head 12, as illustrated in FIG. 7.

The pressing head 4 is then assigned to the twist 38 of the packing tube 13 (FIG. 7). In the following step of the process the depression 29 of the shaped member 28, which is heated by means of the resistance heating element 31, is brought axially up to the twist rosette 39 (FIG. 8) and then, during a relative rotary movement between the winding spindle 1 and the pressing head 4, is pressed against the push-off head 12, as can be seen in FIG. 9. The cylindrical outer edge of the twist rosette 39 is thereby folded inwards and, together with the twist neck 40, the twist rosette is pressed against the round dome 42 (FIG. 8) of the packing tube 13.

The packing tube 13, which at one end is thus provided with a substantially smooth-surfaced round dome 42, is then, afer removal of the pressing head 4, pushed off the winding spindle 1 by the push-off head 12 through the axial movement of the push-off rod 11 in the direction of the push-off head 12, and then, as shown in FIG. 10, is placed in a cavity 43 in a conveyor means 44.

By suitably holding the packing tube 13 fast in the conveyor means 44, and drawing back the push-off rod 11 together with the push-off head 12 into the starting position relative to the winding spindle 1, the packing tube 13 is prepared for further processing, e.g. the insertion of a tampon.

I claim:

1. A method for producing a cylindrical packing tube, open at one end and closed at the other and intended, in particular, for enclosing tampons used in female hygiene, wherein said tube is provided with a gripping tab to facilitate the tearing open of the final packed tube, said method comprising;

providing a generally rectangular sheet material for rolling into a cylindrical tube, said sheet having ends and having first and second edges; said first edge having a non-linear contour shaped to have a projecting tab and said second edge having a non-linear contour shaped to have an indentation, said contours of said edges being parallel;

providing a hollow cylindrical winding spindle having suction apertures arranged along its cylindrical wall in a pattern having a non-linear contour identical to the contour of the second edge of said sheet;

introducing said second edge of said sheet tangentially to the cylindrical wall of said winding spindle with said second edge generally parallel to the axis of said winding spindle;

applying suction to said apertures to draw the portion of the sheet adjacent to the second edge onto the spindle;

winding the spindle to form the cylinder with the portion of the sheet adjacent to the first parallel edge overlapping a portion of the sheet adjacent to the second parallel edge; and heat sealing said overlapped portions.

2. The method of claim 1 wherein said sheet is first cut from a long strip of packing material and led to said winding spindle with the leading edge of said cut sheet being the second edge and the trailing edge of said cut sheet being the first edge.

3. The method of claim 1 wherein said sheet is introduced to the wall of said winding spindle with a first end projecting beyond a first end of said winding spindle.

4. The method of claim 3 wherein, after said sheet is wound and heat sealed, said projecting end is sealed.

5. The method of claim 4 wherein said end is sealed by twisting said end.

6. The method of claim 5 wherein said twisting is accomplished by gripping the extreme end portions of said end and rotating said end portions relative to said remaining wound sheet to form a twist with a twist rosette and a twist neck.

7. The method of claim 6 wherein a bearing surface is provided at said first end of said winding spindle and said rosette is pressed against said bearing surface.

* * * * *